(12) United States Patent
Mallo

(10) Patent No.: US 7,771,710 B2
(45) Date of Patent: *Aug. 10, 2010

(54) POWDERED POLYMER, METHOD FOR ITS PREPARATION, AND USE AS A THICKENER

(75) Inventor: Paul Mallo, Croissy sur Seine (FR)

(73) Assignee: Societe d'Exploitation de Produits pour les Industries Chimiques, Paris (FR)

( * ) Notice: Subject to any disclaimer, the term of this patent is extended or adjusted under 35 U.S.C. 154(b) by 1773 days.

This patent is subject to a terminal disclaimer.

(21) Appl. No.: 10/877,203

(22) Filed: Jun. 25, 2004

(65) Prior Publication Data

US 2005/0002977 A1 Jan. 6, 2005

(30) Foreign Application Priority Data

Jun. 26, 2003 (FR) .................. 03 50261

(51) Int. Cl.
*A61K 8/81* (2006.01)
*A61K 8/02* (2006.01)

(52) U.S. Cl. ............. 424/70.16; 424/401; 514/844; 514/938; 514/939

(58) Field of Classification Search ............... 424/70.16, 424/401; 514/844, 938, 939
See application file for complete search history.

(56) References Cited

U.S. PATENT DOCUMENTS

| | | | |
|---|---|---|---|
| 2,798,053 A | 7/1957 | Brown | |
| 4,423,199 A | 12/1983 | Chang et al. | |
| 5,368,850 A | 11/1994 | Cauwet et al. | |
| 5,373,044 A | 12/1994 | Adams et al. | |
| 5,458,881 A | 10/1995 | Berger et al. | |
| 5,470,551 A | 11/1995 | Dubief et al. | |
| 5,670,471 A | 9/1997 | Amalric et al. | |
| 5,679,656 A | 10/1997 | Hansenne | |
| 5,888,482 A | 3/1999 | Amalric et al. | |
| 5,958,431 A | 9/1999 | Brancq et al. | |
| 6,024,946 A | 2/2000 | Dubief et al. | |
| 6,197,287 B1 * | 3/2001 | Mallo et al. | 424/70.16 |
| 6,346,239 B1 * | 2/2002 | Mallo et al. | 424/70.16 |
| 6,353,034 B1 | 3/2002 | Amalric et al. | |
| 6,437,068 B2 | 8/2002 | Löffler et al. | |
| 6,645,476 B1 | 11/2003 | Morschhäuser et al. | |
| 2004/0028637 A1 * | 2/2004 | Villard et al. | 424/70.16 |

FOREIGN PATENT DOCUMENTS

| | | | |
|---|---|---|---|
| DE | 195 23 596 A1 | 1/1997 | |
| EP | 0 161 038 | * | 11/1985 |
| EP | 0 161 038 A1 | 11/1985 | |
| EP | 0 301 532 A2 | 2/1989 | |
| EP | 0 576 188 | 12/1993 | |
| EP | 0 603 019 A1 | 6/1994 | |
| EP | 0 629 396 B1 | 12/1994 | |
| EP | 0 684 024 | 11/1995 | |
| EP | 0 604 249 | 4/1997 | |
| EP | 0 715 845 | 8/1997 | |
| EP | 1 069 142 A1 | 1/2001 | |
| EP | 1 116 73 A1 | 7/2001 | |
| EP | 0 939 670 B1 | 8/2001 | |
| EP | 0 816 403 B1 | 5/2004 | |
| FR | 2 734 496 | 11/1996 | |
| FR | 2 782 086 | 2/2000 | |
| FR | 2 786 493 | 2/2000 | |
| FR | 2 787 457 | 6/2000 | |
| FR | 2 789 395 | 8/2000 | |
| FR | 2 810 545 | 12/2001 | |
| WO | WO 92 06778 | 4/1992 | |
| WO | WO 92 21316 | 12/1992 | |
| WO | WO 92 21318 | 12/1992 | |
| WO | WO 93 05762 | 4/1993 | |
| WO | WO 93 07856 | 4/1993 | |
| WO | WO 93 07902 | 4/1993 | |
| WO | WO 93 08204 | 4/1993 | |
| WO | WO 93 21316 | 10/1993 | |
| WO | WO 94 27561 | 12/1994 | |
| WO | WO 95 04592 | 2/1995 | |
| WO | WO 95 13863 | 5/1995 | |
| WO | WO 96 37285 | 11/1996 | |
| WO | WO 97 02006 | 1/1997 | |
| WO | WO 98 09611 | 3/1998 | |
| WO | WO 98 22207 | 5/1998 | |
| WO | WO 98 47610 | 10/1998 | |
| WO | WO 00 32639 | 6/2000 | |

OTHER PUBLICATIONS

International Search Report for PCT/FR03/50261.

* cited by examiner

*Primary Examiner*—Johann R Richter
*Assistant Examiner*—Abigail Fisher
(74) *Attorney, Agent, or Firm*—Young & Thompson

(57) ABSTRACT

A composition, which may be used as an emulsifier or thickening agent for cosmetic and topical products, and its method of production. The composition is based upon one or more anionic polyelectrolytes formed from monomers with an acid functional group. The acid group may be a strong acid or weak acid, and partially or completely salified. A neutral monomer may also be present. Additionally, the composition includes one or more emulsifiers of the water-in-oil type and water.

29 Claims, No Drawings

POWDERED POLYMER, METHOD FOR ITS PREPARATION, AND USE AS A THICKENER

This is a U.S. utility application that claims priority to French application No. 03/50261, filed Jun. 26, 2003.

BACKGROUND OF THE INVENTION

The cosmetics industry and the pharmaceutical industry very regularly use synthetic thickening polymers to increase the viscosity of creams, emulsions and various topical solutions. The synthetic thickening polymers currently used in these fields are provided in two physical forms, the powdered form and the liquid form for which the polymer is dispersed in an oil with the aid of surfactants and which is commonly called invert latex.

The most widely known thickening polymers in powdered form are the polymers based on acrylic acid and the copolymers based on acrylic acid and its esters. There may be mentioned for example the polymers marketed by the company Noveon under the trade name CARBOPOL™ and PEMULEN™. They are described in particular in American patents U.S. Pat. No. 5,373,044, U.S. Pat. No. 2,798,053 and in European patent EP 0 301 532.

In cosmetics, homopolymers or copolymers based on 2-acrylamido-2-methyl-propanesulphonic acid are also and always used in powdered form. These thickening polymers are marketed under the trade name Aristoflex™ and are described in particular in European patents EP 816 403, EP 1 116 733 and EP 1 069 142. These thickeners in powdered form are obtained by precipitation polymerization, which triggers numerous successive steps of purification of the final product in order to remove therefrom any trace of residual solvent.

Self-reversible invert latexes do not exhibit this disadvantage and are very rapidly dispersed in water. On the other hand, they contain a lot of oil and one or more surfactants which, in some cases, cause skin intolerance reactions. However, this problem has not yet been fully satisfactorily solved by the mere replacement of one oil by another. Furthermore, self-reversible invert latexes do not allow the preparation of clear gels.

The applicant has therefore searched for novel thickening systems which do not have the disadvantages mentioned above while having adequate thickening properties for them to be an acceptable alternative to the compositions of the state of the art.

BRIEF SUMMARY OF THE INVENTION

The subject of the invention is a composition comprising:
(a) from 80% to 99% by weight of at least one anionic polyelectrolyte chosen from:
  branched or crosslinked homopolymers of a monomer possessing a partially or completely salified strong acid functional group,
  branched or crosslinked homopolymers of a monomer possessing a partially or completely salified weak acid functional group,
  branched or crosslinked copolymers of monomers possessing a partially or completely salified strong acid functional group,
  branched or crosslinked copolymers of monomers possessing a partially or completely salified weak acid functional group,
  branched or crosslinked copolymers of monomers possessing a partially or completely salified strong acid functional group and either of at least one monomer possessing a partially or completely salified weak acid functional group and/or of at least one neutral monomer, and
  branched or crosslinked copolymers of monomers possessing a partially or completely salified weak acid functional group and at least one neutral monomer,
(b) from 1% to 20% by weight of at least one emulsifier of the water-in-oil (W/O) type, and
(c) up to 19% by weight of water.

DETAILED DESCRIPTION OF THE INVENTION

The subject of the invention is a composition comprising:
(a) from 80% to 99% by weight of at least one anionic polyelectrolyte chosen from:
  branched or crosslinked homopolymers of a monomer possessing a partially or completely salified strong acid functional group,
  branched or crosslinked homopolymers of a monomer possessing a partially or completely salified weak acid functional group,
  branched or crosslinked copolymers of monomers possessing a partially or completely salified strong acid functional group,
  branched or crosslinked copolymers of monomers possessing a partially or completely salified weak acid functional group,
  branched or crosslinked copolymers of monomers possessing a partially or completely salified strong acid functional group and either of at least one monomer possessing a partially or completely salified weak acid functional group and/or of at least one neutral monomer, and
  branched or crosslinked copolymers of monomers possessing a partially or completely salified weak acid functional group and at least one neutral monomer,
(b) from 1% to 20% by weight of at least one emulsifier of the water-in-oil (W/O) type, and
(c) up to 19% by weight of water.

The expression branched polymer denotes a nonlinear polymer which possesses pendant chains so as to obtain, when this polymer is dissolved in water, a high degree of entanglement leading to very high viscosities at a low speed gradient.

The expression crosslinked polymer denotes a nonlinear polymer which exists in the state of a three-dimensional network insoluble in water, but swellable in water and therefore leading to the obtaining of a chemical gel.

The composition according to the invention may contain crosslinked units and/or branched units.

The strong acid functional group of the monomer containing it is in particular the sulphonic acid functional group or the phosphonic acid functional group, partially or completely salified. The said monomer may be for example partially or completely salified styrene sulphonic acid or preferably partially or completely salified 2-methyl-2-[(1-oxo-2-propenyl)amino]-1-propanesulphonic acid, in particular in the form either of an alkali metal salt such as for example the sodium salt or the potassium salt, or of an ammonium salt, or the salt of an amino alcohol such as for example the monoethanolamine salt or the salt of an amino acid such as for example the lysine salt.

The weak acid functional group of the monomer containing it is in particular the carboxylic acid functional group, and preferably the said monomer is chosen from acrylic acid, methacrylic acid, itaconic acid, maleic acid or 3-methyl-3-

[(1-oxo-2-propenyl)amino]butanoic acid, the said acids being partially or completely salified, in particular in the form either of an alkali metal salt such as for example the sodium salt or the potassium salt, or of an ammonium salt, or the salt of an amino alcohol such as for example the monoethanolamine salt or the salt of an amino acid such as for example the lysine salt.

The neutral monomer is chosen in particular from acrylamide, methacrylamide, dimethyl acrylamide, (2-hydroxyethyl) acrylate, (2,3-dihydroxypropyl) acrylate, (2-hydroxyethyl) methacrylate, (2,3-dihydroxypropyl) methacrylate, diacetone acrylamide or an ethoxylated derivative, having a molecular weight of between 400 and 1000, of each of these esters.

The expression "emulsifier of the water-in-oil type" denotes surfactants having an HLB value which is sufficiently low to provide water-in-oil emulsions such as surfactant polymers of the polyethylene glycol poly(hydroxystearic acid) block copolymer type, which are marketed by the applicant under the name Simaline™ IE 200, such as the sorbitan esters like the sorbitan monooleate marketed by the applicant under the name MONTANE™ 80, the sorbitan isostearate marketed by the applicant under the name MONTANE™ 70, the sorbitan oleate ethoxylated with 5 moles of ethylene oxide (5 EO) marketed by the applicant under the name MONTANE™ 81, the diethoxylated (2 EO) oleocetyl alcohol marketed by the applicant under the name SIMULSOL™ OC 72 or the sorbitan sesquioleate marketed by the applicant under the name MONTANE™ 83.

The expression "up to 19% by weight of water" indicate that the composition as defined above comprises a non zero quantity of water.

The composition as defined above often comprises less than 10% by weight of emulsifier of the water-in-oil type.

The composition as defined above comprises more particularly at least 0.5% by weight of water and frequently at least 2% by weight of water.

The composition as defined above comprises more particularly less than 10% by weight of water.

The composition which is the subject of the present invention is provided in powdered form.

According to a first embodiment of the present invention, the composition as defined above additionally comprises:
(d) up to 19% by weight of at least one emulsifier of the oil-in-water (O/W) type.

The expression "emulsifier of the oil-in-water type" denotes surfactants having an HLB value which is sufficiently high to provide oil-in-water emulsions, such as ethoxylated sorbitan esters like the sorbitan oleate ethoxylated with 20 moles of ethylene oxide (20 EO), marketed by the applicant under the name MONTANOX™ 80, the castor oil ethoxylated with 40 moles of ethylene oxide (40 EO), marketed by the applicant under the name SIMULSOL™ OL 50, the sorbitan oleate ethoxylated with 20 moles of ethylene oxide (20 EO), marketed by the applicant under the name MONTANOX™ 20, the sorbitan trioleate ethoxylated with 25 moles, marketed by the applicant under the name MONTANOX™ 85, the lauryl alcohol ethoxylated with 7 moles of ethylene oxide (7 EO), marketed by the applicant under the name SIMULSOL™ P 7, the decaethoxylated (10 EO) oleocetyl alcohol marketed by the applicant under the name SIMULSOL™ OC 710 or the polyethoxylated sorbitan hexaoleates marketed under the names G-1086™ and G-1096™.

The composition as defined above often comprises less than 10% by weight of emulsifier of the oil-in-water type.

According to a second particular embodiment of the present invention, the composition as defined above additionally comprises:
(e) up to 19% by weight of oil.

This oil is generally a commercial mineral oil containing saturated hydrocarbons such as paraffins, isoparaffins and cycloparaffins, having, at room temperature, a density of between 0.7 and 0.9, such as for example ISOPAR™ G, ISOPAR™ H, ISOPAR™ I, ISOPAR™ J, ISOPAR™ L, ISOPAR™ M, EXXOL™ D 100 S or MARCOL™ 52 marketed by EXXON CHEMICAL, isohexadecane or isododecane, either a synthetic oil, or a mixture of several of these oils.

Isohexadecane, which is identified in Chemical Abstracts by the number RN=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is marketed in France by the company BAYER.

MARCOL™ 52 is a commercial oil corresponding to the definition of the liquid paraffins of the French Codex. It is a white mineral oil conforming to the regulations FDA 21 CFR 172.878 and CFR 178.3620 (a) and it is contained in the US pharmacopoeia, US XXIII (1995) and in the European pharmacopoeia (1993).

Hydrogenated polyisobutene is marketed in France by the company Ets B. Rossow and Co. under the name PARLEAN-POLYSYNLANE™. It is cited in Michel and Irene Ash; Thesaurus of Chemical Products, Chemical Publishing Co, Inc. 1986, Volume I, page 211 (ISBN 0 7131 3603 0).

Squalane is marketed in France by the company SOPHIM, under the name PHYTOSQUALAN™. It is identified in Chemical Abstracts by the number RN=111-01-3. It is a mixture of hydrocarbons containing more than 80% by weight of 2,6,10,15,19,23-hexamethyltetracosane.

The composition as defined above often comprises less than 5% by weight of oil.

According to a third particular embodiment, the subject of the invention is a composition as defined above, characterized in that the anionic polyelectrolyte is crosslinked and/or branched with a diethylene or polyethylene compound in the molar proportion, expressed relative to the monomers used, of 0.005% to 1%, and preferably 0.01% to 0.5%, and more particularly 0.01% to 0.25%, preferably that for which the crosslinking agent and/or branching agent is chosen from ethylene glycol dimethacrylate, diallyloxyacetic acid or one of its salts such as sodium diallyloxyacetate, ethylene glycol diacrylate, diallylurea, triallylamine, trimethylol propanetriacrylate or methylenebis(acrylamide) or a mixture of its compounds.

The composition as defined above may also comprise various additives such as complexing agents, transfer agents or chain regulator agents.

The subject of the invention is more particularly the composition as defined above, in which the anionic polyelectrolyte is chosen from the following polymers:
copolymer of acrylic acid partially salified in the form of an alkali metal salt or of an ammonium salt and of acrylamide, crosslinked with methylenebis(acrylamide);
copolymer of 2-methyl-2-[(1-oxo-2-propenyl)amino]-1-propanesulphonic acid partially salified in the form of an alkali metal salt or of an ammonium salt and of acrylamide, crosslinked with methylenebis(acrylamide);
copolymer of 2-methyl-2-[(1-oxo-2-propenyl)amino]-1-propanesulphonic acid partially salified in the form of a sodium salt and of acrylic acid partially salified in the form of an alkali metal salt or of an ammonium salt, crosslinked with methylenebis-(acrylamide);

copolymer of 2-methyl-2-[(1-oxo-2-propenyl)amino]-1-propanesulphonic acid partially salified in the form of an alkali metal salt or of an ammonium salt and of 2-hydroxyethyl acrylate, crosslinked with methylenebis(acrylamide);

homopolymer of 2-methyl-2-[(1-oxo-2-propenyl)amino]-1-propanesulphonic acid partially salified in the form of an alkali metal salt or of an ammonium salt, crosslinked with methylenebis(acrylamide);

homopolymer of acrylic acid partially salified in the form of an ammonium salt or of a monoethanolamine salt, crosslinked with sodium diallyloxyacetate; or homopolymer of acrylic acid partially salified in the form of an ammonium salt or of a monoethanolamine salt, crosslinked with triallylamine.

The subject of the invention is also a method for preparing the composition as defined above, characterized in that:
(a) an aqueous solution containing the monomers and the optional additives is emulsified in an oil phase in the presence of one or more emulsifying agents of the water-in-oil type,
(b) the polymerization reaction is initiated by introducing into the emulsion formed in a) a free-radical initiator and then it is allowed to proceed, and
(c) when the polymerization reaction is complete, the polymer emulsion formed is spray-dried.

The spray-drying technique consists in creating a cloud of fine droplets of emulsions in a stream of hot air for a controlled period. An apparatus of the Niro™ type may be advantageously used.

Spray-drying equipment is described in detail in "Spray drying Handbook" by K. Master, 5th Ed, Longman Scientific 1991.

According to a preferred embodiment of the method as defined above, the polymerization reaction is initiated by an oxidation-reduction pair, at a temperature of less than or equal to 20° C., and then carried out either in a practically adiabatic manner up to a temperature greater than or equal to 40° C., more particularly greater than or equal to 50° C., or by regulating the variation in temperature.

The subject of the invention is also a variant of the method as defined above, comprising a step (b') during which one or more emulsifying agents of the oil-in-water type are added to the reaction medium obtained from step (b), before carrying out step (c).

The subject of the invention is also a variant of the method as defined above, according to which the reaction medium obtained from step (b) or from step (b') is concentrated by distillation before carrying out step (c).

The subject of the invention is also a method for preparing the composition as defined above, characterized in that there is spray-dried a self-reversible invert latex:
of 15% to 40% by weight, and preferably of 20% to 25% by weight of oil,
of 20% to 50% of water,
of 2.5% to 15% by weight, and preferably of 4% to 9% by weight of emulsifiers, of which 20% to 50%, in particular 25% to 40%, of the total weight of emulsifiers present are of the water-in-oil (W/O) type and of which 80% to 50%, in particular 75% to 60%, of the total weight of emulsifiers are of the oil-in-water (O/W) type, and
of 20% to 70% by weight, and preferably of 25% to 50% by weight, of a branched or crosslinked anionic polyelectrolyte chosen from:
branched or crosslinked homopolymers of a monomer possessing one partially or completely salified strong acid functional group,
branched or crosslinked homopolymers of a monomer possessing a partially or completely salified weak acid functional group,
branched or crosslinked copolymers of monomers possessing a partially or completely salified strong acid functional group,
branched or crosslinked copolymers of monomers possessing a partially or completely salified weak acid functional group,
branched or crosslinked copolymers of monomers possessing a partially or completely salified strong acid functional group and either of at least one monomer possessing a partially or completely salified weak acid functional group and/or of at least one neutral monomer, and
branched or crosslinked copolymers of monomers possessing a partially or completely salified weak acid functional group and of at least one neutral monomer.

Among the self-reversible invert latexes appropriate for carrying out the method as defined above, there are for example the compositions marketed under the trademarks:

SEPIGEL™ 305 (INCI name: Polyacrylamide and C13-C14 Isoparaffin and Laureth-7),

SIMULGEL™ EG (INCI name: Sodium acrylate and Acryloyldimethyl Taurate Copolymer and Isohexadecane and Polysorbate 80), SIMULGEL™ NS (INCI name: Hydroxyethyl Acrylate and Sodium Acryloyldimethyl Taurate Copolymer and Squalane and Polysorbate 60), SIMULGEL™ A (INCI name: Ammonium Polyacrylate and Isohexadecane and Polysorbate 89), SIMULGEL™ 600 (INCI name: Acrylamide and Sodium Acryloyldimethyl Taurate Copolymer and Polysorbate 80), SIMULGEL™ 800 (INCI name: Sodium Polyacryloyldimethyl Taurate and Isohexadecane and Sorbitan oleate), SIMULGEL™ HT (Polyacrylamide and paraffin oil and Polysorbate 80), and SIMULGEL EPG™ (INCI name: Sodium Acrylate and Acryloyldimethyl Taurate copolymer and Polyisobutene and Caprylyl capryl Glucoside).

The subject of the invention is also the use of the composition as defined above as thickener and/or as emulsifier, of a cosmetic, dermopharmaceutical or pharmaceutical topical composition.

A topical composition according to the invention, intended to be applied to the skin or the mucous membranes of humans or of animals, may consist of a topical emulsion comprising at least one aqueous phase and at least one oily phase. This topical emulsion may be of the oil-in-water type. More particularly, this topical emulsion may consist of a fluid emulsion, such as a milk or a fluid gel. The oily phase of the topical emulsion may consist of a mixture of one or more oils.

A topical composition according to the invention may be intended for cosmetic use or may be used to prepare a medicament intended for the treatment of diseases of the skin and of the mucous membranes. In the latter case, the topical composition then comprises an active ingredient which may for example consist of an antiinflammatory agent, a muscle relaxant, an antifungal or an antibacterial.

When the topical composition is used as a cosmetic composition intended to be applied to the skin or the mucous membranes, it may or may not contain an active ingredient, for example a moisturizing agent, a tanning agent, a sunscreen, an antiwrinkle agent, a slimming agent, an anti-free-radical agent, an antiacne agent or an antifungal.

A topical composition according to the invention usually contains between 0.1% and 10% by weight of thickening agent defined above. The pH of the topical composition is preferably greater than or equal to 5.

The topical composition may additionally contain compounds which are conventionally included in this type of compositions, for example perfumes, preservatives, colorants, emollients or surfactants.

According to yet another aspect, the invention relates to the use of a novel thickening agent in accordance with the invention mentioned above, for thickening or emulsifying a topical composition comprising at least one aqueous phase.

The composition according to the invention is an advantageous substitute for those sold under the name SEPIGEL™ 305 or SEPIGEL™ 501, SIMULGEL™ EG, SIMULGEL™ NS SIMULGEL™ 600 or SIMULGEL™ A by the applicant, because it also exhibits good compatibility with the other excipients used for the preparation of formulations such as milks, lotions, creams, soaps, baths, balms, shampoos or conditioners. It can also be used with the said SEPIGEL™ or SIMULGEL™.

It is in particular compatible with the concentrates described and claimed in international publications WO 92/06778, WO 95/04592, WO 95/13863, WO 96/37285, WO 98/22207, WO 98/47610 or in FR 2 734 496, with the surfactants described in WO 93/08204.

It is particularly compatible with MONTANOV™ 68, MONTANOV™ 82, MONTANOV™ 202 or SEPIPERL™ N. It may also be used in emulsions such as those described and claimed in EP 0 629 396 and in cosmetically or physiologically acceptable aqueous dispersions with an organopolysiloxane compound chosen for example from those described in WO 93/05762 or in WO 93/21316.

It may also be used to form cosmetically or physiologically acceptable aqueous gels at acidic pH, such as those described in WO 93/07856; it may also be used in combination with nonionic celluloses to form for example hair-styling gels such as those described in EP 0 684 024, or alternatively in combination with esters of fatty acids and of a sugar, to form compositions for the treatment of hair or of the skin, such as those described in EP 0 603 019, or alternatively in shampoos or conditioners as described and claimed in WO 92/21316 or finally in combination with an anionic homopolymer such as CARBOPOL™ to form products for treating hair such as those described in DE 19523596.

The composition according to the invention is also compatible with active ingredients such as for example self-tanning agents such as dihydroxyacetone (DHA) or anti-acne agents; it can therefore be introduced into self-tanning compositions such as those claimed in EP 0 715 845, EP 0 604 249, EP 0 576 188 or in WO 93/07902.

It is also compatible with the N-acylated derivatives of amino acids, which allows its use in soothing compositions, in particular for sensitive skin, such as those described or claimed in WO 92/21318, WO 94/27561 or WO 98/09611.

EXAMPLES

The following examples illustrate the invention without however limiting it.

Example A

Comparative Example

Preparation of a Composition A without Inverting Agent

The following are loaded into a beaker, with stirring:
85.5 g of deionized water
95.0 of an aqueous sodium hydroxide solution at 48% (by weight)
246.7 g of 2-methyl-2-[(1-oxo-2 propenyl) amino]-1-propanesulphonic acid
253.8 g of acrylamide 50% w/w in water,
0.18 g of sodium diethylenetriaminepentaacetate,
0.61 g of triallylamine, and
0.34 g of ammonium persulphate.

The pH of the aqueous phase described above is adjusted to 5.2 and the quantity of aqueous phase is adjusted up to a quantity of 682 g by addition of deionized water.

In parallel, an organic phase is prepared by successively introducing into a stirred beaker:
220 g of ISOPAR™ M
27.5 g of MONTANE™ 70 (sorbitol isostearate marketed by Tepic).

The aqueous phase is gradually introduced into the organic phase and then subjected to vigorous mechanical stirring of the Ultra-Turrax™ type marketed by IKA.

The emulsion obtained is then transferred to a polymerization reactor. The emulsion is subjected to considerable nitrogen bubbling so as to remove the oxygen and cooled to about 5-6° C.

After a period sufficient for good homogenization of the solution, an aqueous sodium metabisulphite solution is then introduced (0.2 g in 100 ml of water) in an amount of 0.5 ml/minute. The introduction is carried out for about 60 minutes.

During this introduction, the temperature in the polymerization reactor is allowed to rise up to the final polymerization temperature.

The reaction medium is then maintained for about 90 minutes at this temperature.

The whole is cooled to a temperature of about 35° C. and the composition A is obtained.

Example B

Comparative Example

Preparation of a Composition B with Inverting Agent

The following are loaded into a beaker, with stirring:
85.5 g of deionized water
95.0 of an aqueous sodium hydroxide solution at 48% (by weight)
246.7 g of 2-methyl-2-[(1-oxo-2 propenyl) amino]-1-propanesulphonic acid
253.8 g of acrylamide 50% w/w in water,
0.18 g of sodium diethylenetriaminepentaacetate,
0.61 g of triallylamine, and
0.34 g of ammonium persulphate.

The pH of the aqueous phase described above is adjusted to 5:2 and the quantity of aqueous phase is adjusted up to a quantity of 682 g by addition of deionized water.

In parallel, an organic phase is prepared by successively introducing into a stirred beaker:
220 g of ISOPART™ M
27.5 g of MONTANE™ 70 (sorbitol isostearate marketed by SEPPIC).

The aqueous phase is gradually introduced into the organic phase and then subjected to vigorous mechanical stirring of the Ultra-Turrax™ type marketed by IKA.

The emulsion obtained is then transferred to a polymerization reactor. The emulsion is subjected to considerable nitrogen bubbling so as to remove the oxygen and cooled to about 5-6° C.

After a period sufficient for good homogenization of the solution, an aqueous sodium metabisulphite solution is then introduced (0.2 g in 100 ml of water) in an amount of 0.5 ml/minute. The introduction is carried out for about 60 minutes.

During this introduction, the temperature in the polymerization reactor is allowed to rise up to the final polymerization temperature.

The reaction medium is then maintained for about 90 minutes at this temperature.

The whole is cooled to a temperature of about 35° C. and 35 g of Simulsol™ P7 (ethoxylated lauryl alcohol at 7 moles) are slowly added.

The composition B is obtained.

Example 1 a)

Example According to the Invention

Preparation of a Composition 1 without Inverting Agent, According to the Invention The composition A obtained in Example A is spray-dried by means of a Niro™ type apparatus and the composition 1 is obtained in powdered form.

Example 1 b)

Example According to the Invention

Preparation of a Composition 2 with Inverting Agent, According to the Invention

The composition B obtained in Example B is spray-dried by means of a Niro™ type apparatus and the composition 2 is obtained in powdered form.

Analysis and Properties of the Compositions A, B, 1 and 2

Analysis

The contents of each of the constituents of the compositions prepared are presented in the following table:

|  | Composition A | Composition 1 | Composition B | Composition 2 |
|---|---|---|---|---|
| Copolymer | 42.1% | 87% | 40.6% | 81.2% |
| Water | 31.8% | 6.3% | 30.75% | 5.4% |
| ISOPAR M | 23.2% | 0.7% | 22.3% | 0.7% |
| MONTANE 7080 | 2.9% | 6% | 2.8% | 5.6% |
| SIMULSOL ™ P7 | 0% | 0% | 3.55% | 7.1% |
|  | 100% | 100% | 100% | 100% |

Properties

The properties demonstrated for the compositions according to the invention are presented in the following table where they are also put into perspective with those of the original self-reversible invert latexes:

|  | Composition A | Composition 1 | Composition B | Composition 2 |
|---|---|---|---|---|
| Viscosity at 2% in water[1] | 74000 mPas Rotor: No. 6 | n.d. | 72600 mPas Rotor: No. 6 | n.d. |
| Viscosity at 2% in water containing 1% NaCl[1] | 2760 mPas Rotor: No. 3 Speed: 5 revolutions/ minute | n.d. | 1440 mPas Rotor: No. 3 Speed: 5 revolutions/ minute | n.d. |
| Viscosity at 1% in water | n.d. | 79000 mPas Rotor: No. 6 Speed: 5 revolutions/ minute | n.d. | 63400 mPas Rotor: No. 6 Speed: 5 revolutions/ minute |
| Viscosity at 1% in water containing 1% NaCl | n.d. | 3940 mPas Rotor: No. 3 Speed: 5 revolutions/ minute | n.d. | 1580 mPas Rotor: No. 3 Speed: 5 revolutions/ minute |
| Appearance | White gel | Opalescent gel | | Clear gel |
| Gelling time[1] | 1 minute | 1 minute | 1 minute | 1 minute |

[1]The measurements of the viscosity of the composition A (without inverting agent) are carried out in water containing SIMULSOL ™ P7.

These results demonstrate that the compositions in powder form which are the subject of the present invention have properties similar to those of invert latexes, while being easier to use.

Furthermore, an additional trial has shown that the dispersion in water of the powder of the same polymer as that present in compositions 1 and 2, but not combined with any surfactant of the water-in-oil type, caused the formation of a gel but that the expansion of the polymer lasted for about 24 hours.

This demonstrates the importance of combining a polymer, such a surfactant and water in the same spray-dried powder in order to enhance its thickening properties.

The following examples use either of compositions 1 and 2.

Example 2

Care Cream

| | |
|---|---|
| Cyclomethicone: | 10% |
| Composition 1: | 0.8% |
| MONTANOV ™ 68: | 4.5% |
| Preservative: | 0.65% |
| Lysine: | 0.025% |
| EDTA (disodium salt): | 0.05% |
| Xanthan gum: | 0.2% |
| Glycerine: | 3% |
| Water: | qs 100% |

Example 3

Care Cream

| | |
|---|---|
| Cyclomethicone: | 10% |
| Composition 1: | 0.8% |
| MONTANOV ™ 68: | 4.5% |
| Perfluoropolymethyl isopropyl ether: | 0.5% |
| Preservative: | 0.65% |
| Lysine: | 0.025% |
| EDTA (disodium salt): | 0.05% |
| PEMULEN ™ TR: | 0.2% |
| Glycerine: | 3% |
| Water: | qs 100% |

Example 4

Aftershave Balm

Formula

| | | |
|---|---|---|
| A | Composition 1: | 1.5% |
| | Water: | qs 100% |
| B | MICROPEARL ™ M 100: | 5.0% |
| | SEPICIDE ™ CI: | 0.50% |
| | Perfume: | 0.20% |
| | Ethanol 95%: | 10.0% |

Procedure

Add B to A.

Example 5

Satin-Smooth Emulsion for the Body

Formula

| | | |
|---|---|---|
| A | SIMULSOL ™ 165: | 5.0% |
| | LANOL ™ 1688: | 8.50% |
| | Shea butter: | 2% |
| | Paraffin oil: | 6.5% |
| | LANOL ™ 14M: | 3% |
| | LANOL ™ S: | 0.6% |
| B | Water: | 66.2% |
| C | MICROPEARL ™ M 100: | 5% |
| D | Composition 1: | 3% |
| E | SEPICIDE ™ CI: | 0.3% |
| | SEPICIDE ™ HB: | 0.5% |
| | MONTEINE ™ CA: | 1% |
| | Perfume: | 0.20% |
| | Vitamin E acetate: | 0.20% |
| | Sodium pyrolidinone carboxylate: | 1% (moisturizing agent) |

Procedure

Add C to B, emulsify B in A at 70° C., then add D at 60° C. and then E at 30° C.

Example 6

Body Milk

Formula

| | | |
|---|---|---|
| A | SIMULSOL ™ 165: | 5.0% |
| | LANOL ™ 1688: | 12.0% |
| | LANOL ™ 14M: | 2.0% |
| | Cetyl alcohol: | 0.3% |
| | SCHERCEMOL ™ OP: | 3% |
| B | Water: | qs 100% |
| C | Composition 1: | 0.35% |
| D | SEPICIDE ™ CI: | 0.2% |
| | SEPICIDE ™ HB: | 0.5% |
| | Perfume: | 0.20% |

Procedure

Emulsify B in A at around 75° C.; add C at around 60° C., than D at around 30° C.

Example 7

O/W Cream

Formula

| | | |
|---|---|---|
| A | SIMULSOL ™ 65: | 5.0% |
| | LANOL ™ 1688: | 20.0% |
| | LANOL ™ P: | 1.0% (additive with stabilizing effect) |
| B | Water: | qs 100% |
| C | Composition 1: | 2.50% |
| D | SEPICIDE ™ CI: | 0.20% |
| | SEPICIDE ™ HB: | 0.30% |

Procedure

Introduce B into A at around 75° C.; add C at around 60° C., then D at around 45° C.

Example 8

Nongreasy Antisun Gel

Formula

| | | |
|---|---|---|
| A | Composition 1: | 3.00% |
| | Water: | 30% |
| B | SEPICIDE ™ C: | 0.20% |
| | SEPICIDE ™ HB: | 0.30% |
| | Perfume: | 0.10% |
| C | Colorant: | qs |
| | Water: | 30% |
| D | MICROPEARL ™ M 100: | 3.00% |
| | Water: | qs 100% |
| E | Silicone oil: | 2.0% |
| | PARSOL ™ MCX: | 5.00% |

Procedure

Introduce B into A; add C then D then E.

Example 9

Antisun Milk

Formula

| | | |
|---|---|---|
| A | SEPIPERL ™ N: | 3.0% |
| | Sesame oil: | 5.0% |
| | PARSOL ™ MCX: | 5.0% |
| | λ-carragheenan: | 0.10% |
| B | Water: | qs 100% |
| C | Composition 1: | 0.80% |
| D | Perfume: | qs |
| | Preservative: | qs |

Procedure

Emulsify B in A at 75° C. and then add C at around 60° C., then D at around 30° C. and adjust the pH if necessary.

Example 10

Massage Gel

Formula

| | | |
|---|---|---|
| A | Composition 1: | 3.5% |
| | Water: | 20.0% |
| B | Colorant: | 2 drops/100 g |
| | Water: | qs |
| C | Alcohol: | 10% |
| | Menthol: | 0.10% |
| D | Silicone oil: | 5.0% |

Procedure

Add B to A; then add to the mixture C then D.

Example 11

Massage Care Gel

Formula

| | | |
|---|---|---|
| A | Composition 1: | 3.00% |
| | Water: | 30% |
| B | SEPICIDE ™ CI: | 0.20% |
| | SEPICIDE ™ HB: | 0.30% |
| | Perfume: | 0.05% |
| C | Colorant: | qs |
| | Water: | qs 100% |
| D | MICROPEARL ™ SQL: | 5.0% |
| | LANOL ™ 1688: | 2% |

Procedure

Prepare A; add B, then C, then D.

Example 12

Radiance Gel

Formula

| | | |
|---|---|---|
| A | Composition 1: | 4% |
| | Water: | 30% |
| B | ELASTINE ™ HPM: | 5.0% |
| C | MICROPEARL ™ M 100: | 3% |
| | Water: | 5% |
| D | SEPICIDE ™ CI: | 0.2% |
| | SEPICIDE ™ HB: | 0.3% |
| | Perfume: | 0.06% |
| | Sodium pyrrolidinone carboxylate 50%: | 1% |
| | Water: | qs 100% |

Procedure

Prepare A; add B, then C, then D.

Example 13

Body Milk

Formula

| | | |
|---|---|---|
| A | SEPIPERL ™ N: | 3.0% |
| | Glyceryl triheptonate: | 10.0% |
| B | Water: | qs 100% |
| C | Composition 1: | 1.0% |
| D | Perfume: | qs |
| | Preservative: | qs |

Procedure

Melt A at about 75° C. Emulsify B in A at 75° C. and then add C at around 60° C., then D.

Example 14

Make-Up-Removing Emulsion with Sweet Almond Oil

Formula

| | |
|---|---|
| MONTANOV ™ 68: | 5% |
| Sweet almond oil: | 5% |
| Water: | qs 100% |
| Composition 1: | 0.3% |
| Glycerine: | 5% |
| Preservative: | 0.2% |
| Perfume: | 0.3% |

Example 15

Moisturizing Cream for Greasy Skins

Formula

| | |
|---|---|
| MONTANOV ™ 68: | 5% |
| Cetylstearyl octanoate: | 8% |
| Octyl palmitate: | 2% |
| Water: | qs 100% |
| Composition 1: | 0.6% |
| MICROPEARL ™ M100: | 3.0% |
| Mucopolysaccharides: | 5% |
| SEPICIDE ™ HB: | 0.8% |
| Perfume: | 0.3% |

Example 16

Alcohol-Free Soothing Aftershave Balm

Formula

| | |
|---|---|
| Mixture of lauryl amino acids: | 0.1% to 5% |
| Magnesium and potassium aspartate: | 0.002% to 0.5% |
| LANOL ™ 99: | 2% |
| Sweet almond oil: | 0.5% |
| Water: | qs 100% |
| Composition 1: | 3% |
| SEPICIDE ™ HB: | 0.3% |
| SEPICIDE ™ CI: | 0.2% |
| Perfume: | 0.4% |

Example 17

Cream with AHA for Sensitive Skins

Formula

| | |
|---|---|
| Mixture of lauryl amino acids: | 0.1% to 5% |
| Magnesium and potassium aspartate: | 0.002% to 0.5% |
| LANOL ™ 99: | 2% |
| MONTANOV ™ 68: | 5.0% |
| Water: | qs 100% |
| Composition 1: | 1.50% |
| Gluconic acid: | 1.50% |
| Triethanolamine: | 0.9% |
| SEPICIDE ™ HB: | 0.3% |
| SEPICIDE ™ CI: | 0.2% |
| Perfume: | 0.4% |

Example 18

Aftersun Soothing Care

Formula

| | |
|---|---|
| Mixture of lauryl amino acids: | 0.1% to 5% |
| Magnesium and potassium aspartate: | 0.002% to 0.5% |
| LANOL ™ 99: | 10.0% |

-continued

| | |
|---|---|
| Water: | qs 100% |
| Composition 1: | 2.50% |
| SEPICIDE ™ HB: | 0.3% |
| SEPICIDE ™ CI: | 0.2% |
| Perfume: | 0.4% |
| Colorant: | 0.03% |

Example 19

Make-Up-Removing Milk

Formula

| | |
|---|---|
| SEPIPERL ™ N: | 3% |
| PRIMOL ™ 352: | 8.0% |
| Sweet almond oil: | 2% |
| Water: | qs 100% |
| Composition 1: | 0.8% |
| Preservative: | 0.2% |

Example 20

Body Milk

Formula

| | |
|---|---|
| SEPIPERL ™ N: | 3.5% |
| LANOL ™ 37T: | 8.0% |
| SOLAGUM ™ L: | 0.05% |
| Water: | qs 100% |
| Benzophenone: | 2.0% |
| Dimethicone 350 cPs: | 0.05% |
| Composition 1: | 0.8% |
| Preservative: | 0.2% |
| Perfume: | 0.4% |

Example 21

Fluid Emulsion at Alkaline pH

| | |
|---|---|
| MARCOL ™ 82: | 5.0% |
| NaOH: | 10.0% |
| Water: | qs 100% |
| Composition 1: | 1.5% |

Example 22

Fluid Foundation

Formula

| | |
|---|---|
| SIMULSOL ™ 165: | 5.0% |
| LANOL ™ 84D: | 8.0% |

Example 23

Antisun Milk

Formula

| | |
|---|---|
| LANOL™ 99: | 5.0% |
| Water: | qs 100% |
| Inorganic pigments and fillers | 10.0% |
| Composition 1: | 1.2% |
| Preservative: | 0.2% |
| Perfume: | 0.4% |

| | |
|---|---|
| SEPIPERL™ N: | 3.5% |
| LANOL™ 37T: | 10.0% |
| PARSOL™ NOX: | 5.0% |
| EUSOLEX™ 4360: | 2.0% |
| Water: | qs 100% |
| Composition 1: | 1.8% |
| Preservative: | 0.2% |
| Perfume: | 0.4% |

Example 24

Eye Contour Gel

Formula

| | |
|---|---|
| Composition 1: | 2.0% |
| Perfume: | 0.06% |
| Sodium pyrrolidinone carboxylate: | 0.2% |
| DOW CORNING™ 245 fluid | 2.0% |
| Water: | qs 100% |

Example 25

Leave-in Care Composition

Formula

| | |
|---|---|
| Composition 1: | 1.5% |
| Perfume: | qs |
| Preservative: | qs |
| DOW CORNING™ X2 8360: | 5.0% |
| DOW CORNING™ Q2 1401: | 15% |
| Water: | qs 100% |

Example 26

Slimming Gel

| | |
|---|---|
| Composition 1: | 5% |
| Ethanol: | 30% |
| Menthol: | 0.1% |
| Caffeine: | 2.5% |
| Ruscus extract: | 2% |
| Ivy extract: | 2% |
| SEPICIDE™ HB: | 1% |
| Water: | qs 100% |

Example 27

Alcohol-Free Soothing Aftershave Balm

Formula

| | | |
|---|---|---|
| A | LIPACIDE™ PVB: | 1.0% |
| | LANOL™ 99: | 2.0% |
| | Sweet almond oil: | 0.5% |
| B | Composition 1: | 3.5% |
| C | Water: | qs 100% |
| D | Perfume: | 0.4% |
| | SEPICIDE™ HB: | 0.4% |
| | SEPICIDE™ CI: | 0.2% |

Example 28

Aftershave Cooling Gel

Formula

| | | |
|---|---|---|
| A | LIPACIDE™ PVB: | 0.5% |
| | LANOL™ 99: | 5.0% |
| | Composition 1: | 2.5% |
| B | Water: | qs 100% |
| C | MICROPEARL™ LM: | 0.5% |
| | Perfume: | 0.2% |
| | SEPICIDE™ HB: | 0.3% |
| | SEPICIDE™ CI: | 0.2% |

Example 29

Care Product for Greasy Skins

Formula

| | | |
|---|---|---|
| A | MICROPEARL™ M310: | 1.0% |
| | Composition 1: | 5.0% |
| | Octyl isononanoate: | 4.0% |
| B | Water: | qs 100% |
| C | SEPICONTROL™ A5: | 4.0% |
| | Perfume: | 0.1% |
| | SEPICIDE™ HB: | 0.3% |
| | SEPICIDE™ CI: | 0.2% |
| D | CAPIGEL™ 98: | 0.5% |
| | Water: | 10% |

Example 30

Cream with AHAs

Formula

| A | MONTANOV ™ 68: | 5.0% |
|---|---|---|
|   | LIPACIDE ™ PVB: | 1.05% |
|   | LANOL ™ 99: | 10.0% |
| B | Water: | qs 100% |
|   | Gluconic acid: | 1.5% |
|   | TEA (triethanolamine): | 0.9% |
| C | Composition 1: | 1.5% |
| D | Perfume: | 0.4% |
|   | SEPICIDE ™ HB: | 0.2% |
|   | SEPICIDE ™ CI: | 0.4% |

Example 31

Nongreasy Self-Tanning Agent for the Face and the Body

Formula

| A | LANOL ™ 2681: | 3.0% |
|---|---|---|
|   | Composition 1: | 2.5% |
| B | Water: | qs 100% |
|   | Dihydroxyacetone: | 3.0% |
| C | Perfume: | 0.2% |
|   | SEPICIDE ™ HB: | 0.8% |
|   | NaOH (sodium hydroxide): | qs pH = 5% |

Example 32

Antisun Milk with Monoi de Tahiti

Formula

| A | Monoi de Tahiti: | 10% |
|---|---|---|
|   | LIPACIDE ™ PVB: | 0.5% |
|   | Composition 1: | 2.2% |
| B | Water: | qs 100% |
| C | Perfume: | 0.1% |
|   | SEPICIDE ™ HB: | 0.3% |
|   | SEPICIDE ™ CI: | 0.1% |
|   | Octyl methoxycinnamate: | 4.0% |

Example 33

Antisun Care for the Face

Formula

| A | Cyclomethicone and dimethiconol: | 4.0% |
|---|---|---|
|   | Composition 1 | 3.5% |
| B | Water: | qs 100% |
| C | Perfume: | 0.1% |
|   | SEPICIDE ™ HB: | 0.3% |
|   | SEPICIDE ™ CI: | 0.21% |

-continued

| | Octyl methoxycinnamate: | 5.0% |
|---|---|---|
| | Mica-titanium: | 2.0% |
| | Lactic acid: | qs pH = 6.5 |

Example 34

Self-Tanning Emulsion

Formula

| A | LANOL ™ 99: | 15% |
|---|---|---|
|   | MONTANOV ™ 68: | 5.0% |
|   | Octyl para-methoxycinnamate: | 3.0% |
| B | Water: | qs 100% |
|   | Dihydroxyacetone: | 5.0% |
|   | Monosodium phosphate: | 0.2% |
| C | Composition 1 | 0.5% |
| D | Perfume: | 0.3% |
|   | SEPICIDE ™ HB: | 0.8% |
|   | NaOH: | qs pH = 5 |

Example 35

Sheen Gel

| Composition 1 | 1.5% |
|---|---|
| Volatile silicone | 25% |
| Monopropylene glycol | 25% |
| Demineralized water | 10% |
| Glycerine | qs 100% |

Example 36

Slimming Gel

| Composition 1 | 1.5% |
|---|---|
| Isononyl isononanoate | 2% |
| Caffeine | 5% |
| Ethanol | 40% |
| MICROPEARL ™ LM | 2% |
| Demineralized water | qs 100% |
| Preservative perfume | qs |

Example 37

Make-Up-Removing Milk

| SIMULSOL ™ 165 | 4% |
|---|---|
| MONTANOV ™ 202 | 1% |
| Caprylate caprate triglyceride | 15% |
| PECOSIL ™ DCT | 1% |
| Demineralized water | qs |
| CAPIGEL ™ 98 | 0.5% |

-continued

| | |
|---|---|
| Composition 1 | 1% |
| PROTEOL™ OAT | 2% |
| NaOH | qs pH 7 |

Example 38

Antisun Cream

| | |
|---|---|
| SIMULSOL™ 165 | 3% |
| MONTANOV™ 202 | 2% |
| C12-C15 benzoate | 8% |
| PECOSIL™ PS 100 | 2% |
| Dimethicone | 2% |
| Cyclomethicone | 5% |
| Octyl methoxycinnamate | 6% |
| Benzophenone-3 | 4% |
| Titanium oxide | 8% |
| Xanthan gum | 0.2% |
| Butylene glycol | 5% |
| Demineralized water | qs 100% |
| Composition 1 | 1.5% |
| Preservative, perfume | qs |

Example 39

Combination Skin Care Gel

| | |
|---|---|
| Composition 1 | 4% |
| Plant squalane | 5% |
| Dimethicone | 1.5% |
| SEPICONTROL™ A5 | 4% |
| Xanthan gum | 0.3% |
| Water | qs 100% |
| Preservative, perfume | qs |

Example 40

Perfumed Mask for the Body

| | |
|---|---|
| Composition 1 | 1.5% |
| Cyclomethicone | 5% |
| Perfume | 2% |
| MICROPEARL™ M100 | 5% |
| Glycerine | 5% |
| Demineralized water | qs 100% |

Example 41

Cream with Vitamin

| | |
|---|---|
| SIMULSOL™ 165 | 5% |
| MONTANOV™ 202 | 1% |
| Caprylic/capric triglycerides | 20% |

-continued

| | |
|---|---|
| Vitamin A palmitate | 0.2% |
| Vitamin E acetate | 1% |
| MICROPEARL™ M305 | 1.5% |
| Composition 1 | 0.7% |
| Water | qs 100% |
| Preservative, Perfume | qs |

MONTANOV™ 68 (cetearyl glucoside) is a self-emulsifying composition as described in WO 92/06778, marketed by the company SEPPIC.

MICROPEARL™ M 100 is an ultra-fine powder with a very soft feel and with mattifying action, marketed by the company MATSUMO.

SEPICIDE™ CI, imidazolidineurea, is a preservative marketed by the company SEPPIC.

PEMULEN™ TR is an acrylic polymer marketed by GOODRICH.

SIMULSOL™ 165 is self-emulsifying glyceryl stearate marketed by the company SEPPIC.

LANOL™ 1688 is an emollient ester with a non greasy effect marketed by the company SEPPIC.

LANOL™ 14M and LANOL™ S are consistency factors marketed by the company SEPPIC.

SEPICIDE™ HB, which is a mixture of phenoxyethanol, methylparaben, ethylparaben, propylparaben and butylparaben, is a preservative marketed by the company SEPPIC.

MONTEINE™ CA is a moisturizing agent marketed by the company SEPPIC.

SCHERCEMOL™ OP is an emollient ester with a non greasy effect.

LANOL™ P is an additive with a stabilizing effect marketed by the company SEPPIC.

PARSOL™ MCX is octyl para-methoxycinnamate marketed by the company GIVAUDAN.

SEPIPERL™ N is a pearlescent agent marketed by the company SEPPIC, based on a mixture of alkyl polyglucosides such as those described in WO 95/13863.

MICROPEARL™ SQL is a mixture of microparticles containing squalane which is released under the action of massaging; it is marketed by the company MATSUMO.

LANOL™ 99 is isononyl isononanoate marketed by the company SEPPIC.

LANOL™ 37T is glyceryl triheptanoate marketed by the company SEPPIC.

SOLAGUM™ L is a carragheenan marketed by the company SEPPIC.

MARCOL™ 82 is a paraffin oil marketed by the company EXXON.

LANOL™ 84D is dioctyl malate marketed by the company SEPPIC.

PARSOL™ NOX is a sunscreen marketed by the company GIVAUDAN.

EUSOLEX™ 4360 is a sunscreen marketed by the company MERCK.

DOW CORNING™ 245 fluid is cyclomethicone marketed by the company DOW CORNING.

LIPACIDE™ PVB is an acylated wheat protein hydrolysate marketed by the company SEPPIC.

MICROPEARL™ LM is a mixture of squalane, polymethyl methacrylate and menthol marketed by the company SEPPIC.

SEPICONTROL™ A5 is a mixture of capryloyl glycine, sarcosine and Cinnamon zylanicum extract marketed by the company SEPPIC, such as those described in international patent application PCT/FR98/01313 filed on 23 Jun. 1998.

CAPIGEL™ 98 is an acrylic copolymer marketed by the company SEPPIC.

LANOL™ 2681 is a copra caprylate/caprate mixture marketed by the company SEPPIC.

MONTANOV™ 202 is an APG/fatty alcohol composition as described in WO9 98/47610, marketed by the company SEPPIC.

It will be understood that many additional changes in the details which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A composition comprising:
   a) about 80% to about 99% by weight of at least one anionic polyelectrolyte, wherein said polyelectrolyte comprises at least one non-linear polymer member consisting essentially of:
      copolymers of monomers comprising:
         i) a monomer with an at least partially salified strong acid functional group; and
         ii) at least one neutral monomer;
   b) about 1% to about 20% by weight of at least one water-in-oil emulsifier;
   c) up to 19% by weight of water;
   d) up to 19% by weight of at least one oil-in-water emulsifying agent; and
   e) up to 19% by weight of oil.

2. The composition of claim 1, wherein said copolymers comprise at least one member selected from the group consisting of:
   a) crosslinked polymers; and
   b) branched polymers.

3. The composition of claim 1, wherein said salification is complete.

4. The composition of claim 1, comprising less than 10% by weight of said water-in-oil emulsifier.

5. The composition of claim 1, comprising at least about 0.5% by weight of said water.

6. The composition of claim 5, comprising at least about 2% by weight of said water.

7. The composition of claim 1, comprising less than 10% by weight of said water.

8. The composition of claim 1, comprising less than 10% by weight of said oil-in-water emulsifying agent.

9. The composition of claim 1, comprising less than 5% by weight of said oil.

10. The composition of claim 1, wherein said oil comprises at least one member selected from the group consisting of:
    a) white mineral oils;
    b) squalane;
    c) hydrogenated polyisobutene;
    d) octyl palmitate;
    e) isostearyl isostearate;
    f) isododecane; and
    g) isohexadecane.

11. The composition of claim 1, wherein said anionic polyelectrolyte is reacted with a second compound, in a molar ratio expressed relative to the monomers used, of about 0.005% to about 1%.

12. The composition of claim 11, wherein said molar ratio is about 0.01% to about 0.5%.

13. The composition of claim 12, wherein said molar ratio is about 0.01% to about 0.25%.

14. The composition of claim 11, wherein said reacting comprises at least one member selected from the group consisting of:
    a) crosslinking; and
    b) branching.

15. The composition of claim 11, wherein said second compound comprises at least one member selected from the group consisting of:
    a) a diethylene; and
    b) a polyethylene.

16. The composition of claim 11, further comprising a reaction joining agent, said reaction agent comprising at least one member selected from the group consisting of:
    a) ethylene glycol dimethacrylate;
    b) diallyloxacetic acid;
    c) sodium diallyloxyacetate;
    d) ethylene glycol diacrylate;
    e) diallylurea;
    f) triallylamine;
    g) trimethylol propanetriacrylate; and
    h) methylenebis(acrylamide).

17. The composition of claim 1, wherein said at least one non-linear polymer member is selected from the group consisting of:
    a) a copolymer of acrylic acid partially salified in the form of a sodium salt and of acrylamide, crosslinked with methylenebis(acrylamide);
    b) a copolymer of 2-methyl-2-[(1-oxo-2-propenyl)amino]-1-propanesulphonic acid partially salified in the form of a sodium salt and of acrylamide, crosslinked with methylenebis(acrylamide);
    c) a copolymer of 2-methyl-2-[(1-oxo-2-propenyl)amino]-1-propanesulphonic acid partially salified in the form of a sodium salt and of acrylic acid partially salified in the form of a sodium salt, crosslinked with methylene-bis(acrylamide); and
    d) a copolymer of 2-methyl-2-[(1-oxo-2-propenyl)amino]-1-propanesulphonic acid partially salified in the form of a sodium salt and of 2-hydroxyethyl acrylate, crosslinked with methylenebis(acrylamide).

18. A method for preparing a composition, said method comprising:
    a) emulsifying an aqueous solution comprising monomers and additives, in an oil phase, said oil phase comprising at least one water-in-oil emulsifying agent;
    b) creating a reaction medium by initiating a polymerization reaction by introducing into said emulsion a free-radical initiator;
    c) allowing said reaction to proceed to produce a final composition, said final composition comprising:

1) about 80% to about 99% by weight of at least one anionic polyelectrolyte, wherein said polyelectrolyte comprises at least one non-linear polymer member consisting essentially of:
   copolymers of monomers comprising:
      a) a monomer with an at least partially salified strong acid functional group; and
      b) at least one neutral monomer;
2) about 1% to about 20% by weight of at least one water-in-oil emulsifier;
3) up to 19% by weight of water;
4) up to 19% by weight of at least one oil-in-water emulsifying agent; and
5) up to 19% by weight of oil;
d) spray-drying said final composition when said polymerization reaction is complete to form a powder.

19. The method of claim 18, wherein said copolymers further comprise at least one member selected from the group consisting of:
   a) crosslinked polymers; and
   b) branched polymers.

20. The method of claim 18, wherein said salification is complete.

21. The method of claim 18, further comprising adding at least one oil-in-water emulsifying agent to said reaction, said oil-in-water emulsifying agent added after introduction of said initiator and before production of said final composition.

22. The method of claim 18, further comprising concentrating by distillation said reaction medium before said reaction produces said final composition.

23. A method of thickening cosmetic and topical products, said method comprising adding a composition to said products, said composition comprising:
   a) about 80% to about 99% by weight of at least one anionic polyelectrolyte, wherein said polyelectrolyte comprises at least one non-linear polymer member consisting essentially of:
      copolymers of monomers comprising:
         i) a monomer with an at least partially salified strong acid functional group; and
         ii) at least one neutral monomer;
   b) about 1% to about 20% by weight of at least one water-in-oil emulsifier;
   c) up to 19% by weight of water;
   d) up to 19% by weight of at least one oil-in-water emulsifying agent; and
   e) up to 19% by weight of oil.

24. The method of claim 23, wherein said copolymers further comprise at least one member selected from the group consisting of:
   a) crosslinked; and
   b) branched.

25. The method of claim 23, wherein said salification is complete.

26. A method of emulsifying cosmetic and topical products, said method comprising adding a composition to said products, said composition comprising:
   a) about 80% to about 99% by weight of at least one anionic polyelectrolyte, wherein said polyelectrolyte comprises at least one non-linear polymer member consisting essentially of:
      copolymers of monomers comprising:
         i) a monomer with an at least partially salified strong acid functional group; and
         ii) at least one neutral monomer;
   b) about 1% to about 20% by weight of at least one water-in-oil emulsifier;
   c) up to 19% by weight of water;
   d) up to 19% by weight of at least one oil-in-water emulsifying agent; and
   e) up to 19% by weight of oil.

27. The method of claim 26, wherein said copolymers further comprise at least one member selected from the group consisting of:
   a) crosslinked polymers; and
   b) branched polymers.

28. The method of claim 26, wherein said salification is complete.

29. The composition of claim 17, wherein said least one non-linear polymer member is a copolymer of 2-methyl-2-[(1-oxo-2-propenyl)amino]-1-propanesulphonic acid partially salified in the form of a sodium salt and of 2-hydroxyethyl acrylate, crosslinked with methylenebis (acrylamide).

* * * * *

(12) EX PARTE REEXAMINATION CERTIFICATE (9828th)
United States Patent
Mallo

(10) Number: US 7,771,710 C1
(45) Certificate Issued: *Sep. 4, 2013

(54) POWDERED POLYMER, METHOD FOR ITS PREPARATION, AND USE AS A THICKENER

(75) Inventor: Paul Mallo, Croissy sur Seine (FR)

(73) Assignee: Societe d'Exploitation de Produits pour les Industries Chimiques, Quai d'Orsay, Paris (FR)

Reexamination Request:
No. 90/012,735, Dec. 10, 2012

Reexamination Certificate for:
Patent No.: 7,771,710
Issued: Aug. 10, 2010
Appl. No.: 10/877,203
Filed: Jun. 25, 2004

( * ) Notice: This patent is subject to a terminal disclaimer.

(30) Foreign Application Priority Data

Jun. 26, 2003 (FR) ..................................... 03 50261

(51) Int. Cl.
*A61K 8/81* (2006.01)
*A61K 8/02* (2006.01)

(52) U.S. Cl.
USPC ........ 424/70.16; 424/401; 514/844; 514/938; 514/939

(58) Field of Classification Search
None
See application file for complete search history.

(56) References Cited

To view the complete listing of prior art documents cited during the proceeding for Reexamination Control Number 90/012,735, please refer to the USPTO's public Patent Application Information Retrieval (PAIR) system under the Display References tab.

*Primary Examiner* — Evelyn Huang

(57) ABSTRACT

A composition, which may be used as an emulsifier or thickening agent for cosmetic and topical products, and its method of production. The composition is based upon one or more anionic polyelectrolytes formed from monomers with an acid functional group. The acid group may be a strong acid or weak acid, and partially or completely salified. A neutral monomer may also be present. Additionally, the composition includes one or more emulsifiers of the water-in-oil type and water.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-17 and 29 are cancelled.

Claims 18-28 were not reexamined.

\* \* \* \* \*